(12) United States Patent
Fujieda (10) Patent No.: US 6,511,181 B1
(45) Date of Patent: Jan. 28, 2003

(54) DIAGNOSING APPARATUS

(75) Inventor: Masanao Fujieda, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 4 days.

(21) Appl. No.: 09/654,567

(22) Filed: Sep. 1, 2000

(30) Foreign Application Priority Data

Sep. 2, 1999 (JP) .......................................... 11-249037

(51) Int. Cl.$^7$ ................................................. A61B 3/00
(52) U.S. Cl. ....................................................... 351/245
(58) Field of Search ................................ 351/205, 206, 351/208, 245, 246; 257/314, 315, 316; 713/300, 310

(56) References Cited

U.S. PATENT DOCUMENTS

| | | | |
|---|---|---|---|
| 3,883,235 A | * 5/1975 | Lynn et al. ................ | 351/246 |
| 5,463,430 A | 10/1995 | Isogai et al. | |
| 5,563,667 A | 10/1996 | Isogai et al. | |
| 5,584,029 A | * 12/1996 | Izui et al. ................... | 713/300 |
| 5,808,336 A | * 9/1998 | Miyawaki ................... | 257/315 |

* cited by examiner

*Primary Examiner*—George Manuel
(74) *Attorney, Agent, or Firm*—Finnegan, Henderson, Farabow, Garrett & Dunner, L.L.P.

(57) ABSTRACT

A diagnosing apparatus for examining or measuring a body of an examinee, the apparatus comprises an operating part including diagnosing means for examining or measuring the body of the examinee, the operating part is brought into an operable condition by supplying power thereto, data read means for reading out data from a storage medium containing data which is individual to the examinee or to an examiner, condition detecting means for detecting whether or not the data has been read out, or whether or not the data is in a readable condition, and power supply control means for controlling power supply to the operating part based on a result detected by the detecting means.

12 Claims, 5 Drawing Sheets

DIAGNOSING APPARATUS

BACKGROUND OF THE INVENTION

1. Field of the Invention

The present invention relates to a diagnosing apparatus for examining or measuring a body of an examinee.

2. Description of Related Art

Typically, when using a diagnosing apparatus for examining or measuring a body of an examinee (an optometry apparatus such as a visual acuity testing apparatus, an audial acuity testing apparatus, a sphygmomanometer, a body weight and body fat measurement apparatus, or the like), a power switch of the apparatus is turned on to start electrical power supply as motive power of the apparatus. After using the apparatus, the power switch is turned off to suspend the power supply.

Regarding such an apparatus as above, ON/OFF operations of the power switch (especially OFF operations) are important in order not to consume unnecessary power, or not to shorten the lifetime of the components such as a lamp. However, every single ON/OFF operation of the power switch has to be made manually by an examiner or an examinee, which is inconvenient. Especially in the case of an auto diagnosing apparatus which is intended to be operated by an examinee himself without presence of an examiner, it is difficult to have the examinee make ON/OFF operations (especially OFF operations) of the power switch reliably.

To eliminate the inconvenience, there has been suggested an apparatus having a power save mode. This type of apparatus includes a function of suspending power supply to the components, excluding a computer circuit and the like that monitor whether or not the apparatus has been operated, in the case that no operation is made for a predetermined period of time. However, in the case of this type of apparatus, power supply to a computer circuit, which is a part of operating unit, is not suspended. Therefore, it is not regarded that the power consumption is sufficiently reduced.

SUMMARY OF THE INVENTION

The present invention has been made in view of the above circumstances and has an object to overcome the above problems and to provide a diagnosing apparatus which can initiate and suspend power supply with easy operation, and which is capable of saving energy more effectively as well as extending lifetime of the components.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a diagnosing apparatus for examining or measuring a body of an examinee, the apparatus comprises an operating part including diagnosing means for examining or measuring the body of the examinee, the operating part is brought into an operable condition by supplying power thereto, data read means for reading out data from a storage medium containing data which is individual to the examinee or to an examiner, condition detecting means for detecting whether or not the data has been read out, or whether or not the data is in a readable condition, and power supply control means for controlling power supply to the operating part based on a result detected by the condition detecting means.

In another aspect of the present invention, a diagnosing apparatus for examining or measuring a body of an examinee, the apparatus comprises an operating part including diagnosing means for examining or measuring the body of the examinee, the operating part is brought into an operable condition by supplying power thereto, storage means for storing data on the examinee, detecting means for detecting whether or not diagnostic data obtained by the diagnostic means has been stored in the storage means, and power supply control means for controlling power supply to the operating part based on a result detected by the detecting means.

Further, in another aspect of the present invention, a diagnosing apparatus for examining or measuring a body of an examinee, the apparatus comprises an operating part including diagnosing means for examining or measuring the body of the examinee, the operating part is brought into an operable condition by supplying power thereto, output means for outputting diagnostic data on the examinee, detecting means for detecting whether or not the diagnostic data obtained by the diagnosing means has been outputted by the output means, and power supply control means for controlling power supply to the operating part based on a result detected by the detecting means.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
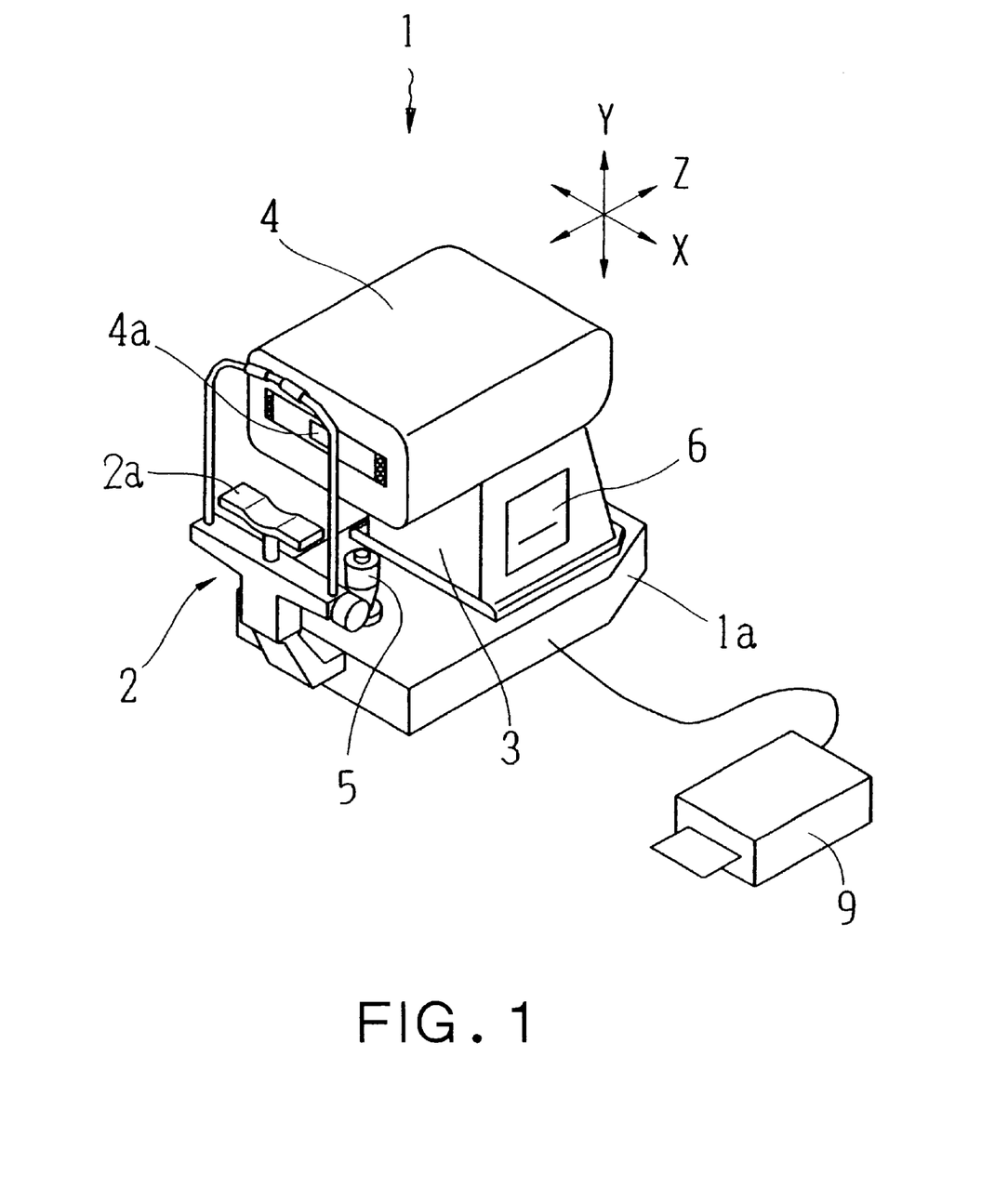
FIG. 1 is a view showing an external representation of an auto visual acuity testing apparatus consistent with one preferred embodiment of a present invention.

A detailed description of one preferred embodiment of a diagnosing apparatus embodying the present invention will now be given referring to the accompanying drawings. FIG. 1 is a view showing an auto visual acuity testing apparatus (an auto refractometer) 1 consistent with the preferred embodiment. The apparatus 1 is constituted such that an examinee can perform a visual acuity test by himself (without presence of an examiner).

Reference numeral 1a is a base. Fixedly attached to the base 1a is a head support unit 2 for fixedly supporting an examinee's head. 3 is a main body and 4 is a measurement unit containing optical systems described later. 5 is a joystick for moving the measurement unit 4. The measurement unit 4 moves in X direction (a lateral direction) relative to the main body 3 by tilting the joystick 5 to right and left, and moves in Y direction (a vertical direction) relative to the main body 3 by titling the joystick 5 back and forth. To be ready for auto alignment, the measurement unit 4 is configured to be movable in X direction, Y direction and Z direction (a back and forth direction) relative to the main body 3 without operating the joystick 5 (description regarding the moving mechanism is given later in detail). 9 is an ID card reader and is connected to the apparatus 1 via a communication cable.

Figure 2:
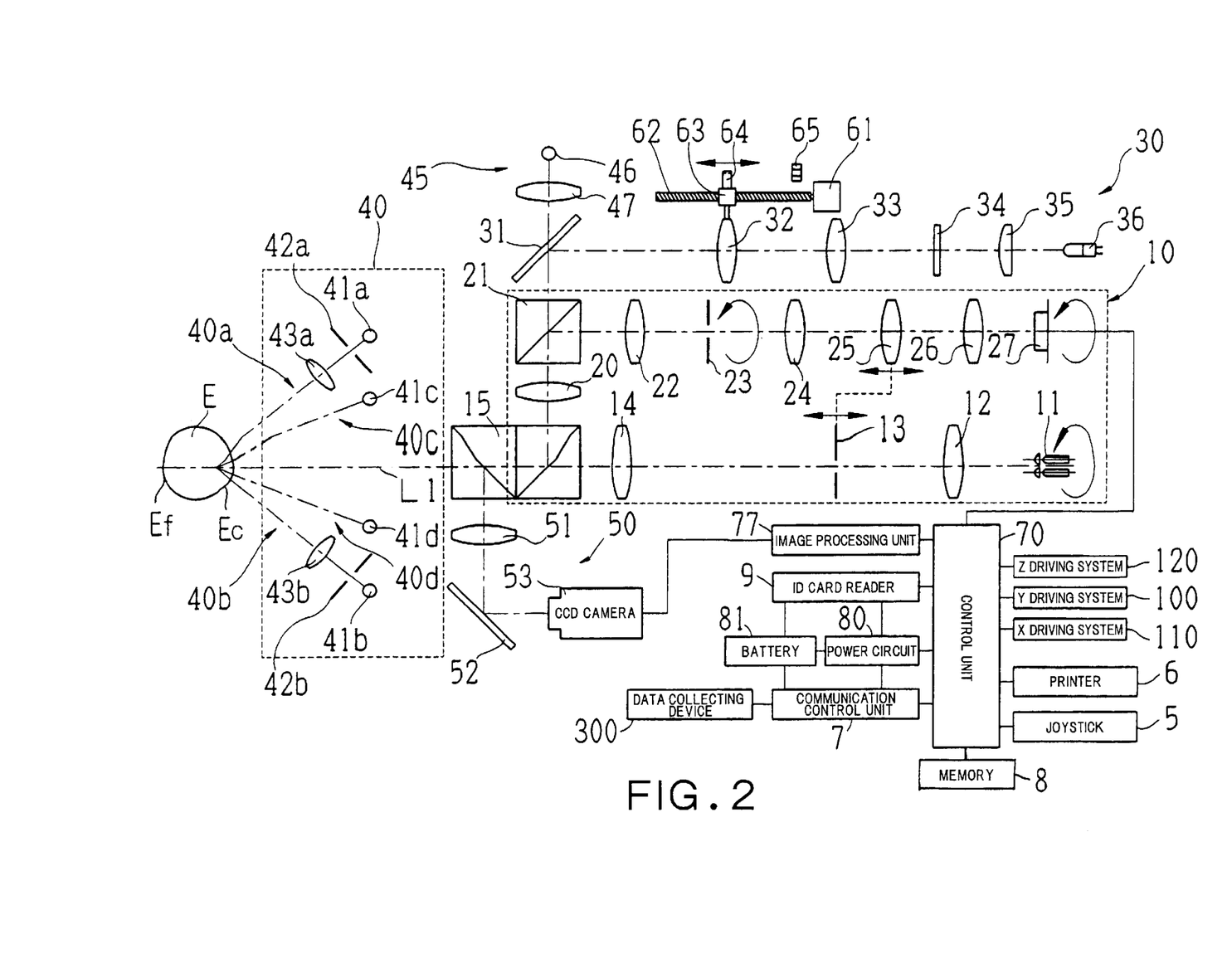
FIG. 2 is a view showing a schematic configuration of optical systems and a control system of the apparatus shown in FIG. 1.

Hereinafter, description is given to a schematic configuration of the optical systems and the control system of the apparatus with reference to FIG. 2.

Optical Systems

Reference numeral 10 is an eye refractive power measurement optical system. 11 is a pair of measurement light sources for emitting near infrared light which is disposed rotatably on a measurement optical axis L1. 12 is a condenser lens. 13 is a target plate which has a spot aperture therethrough, and which is movable along the optical axis L1. 14 is a projection lens, 15 is a beam splitter, 20 is an objective lens, 21 is a beam splitter, and 22 and 24 are relay lenses. 23 is a strip-shaped corneal reflection elimination mask located at a generally conjugate position with a cornea Ec of an eye E to be examined. The mask 23 rotates on an optical axis in synchronism with the optical sources 11. 25 is a mobile lens which moves along the optical axis together with the target plate 13. 26 is an image forming lens. 27 is a photodetector for measurement which rotates on the optical axis in synchronism with the light sources 11 and the mask 23.

Reference numeral 30 is a fixation target optical system. 31 is a half mirror, 32 is a first relay lens which is movable along the optical axis. Movement of the lens 32 along its optical axis causes the eye E to be fogged. To move the lens 32, a pulse motor 61 rotates a feed screw 62 causing a linear motion of a female screw 63 threadedly secured to the screw 62. 64 is a shielding plate and 65 is a photosensor. The photosensor 65 detects an original position (a reset position) of the lens 32 based on a movement of the shielding plate 64. 33 is a second relay lens, and 34 is a fixation target located at a focal point of the lens 33. 35 is a condenser lens and 36 is an illumination lamp.

Reference numeral 45 is a target projection optical system for alignment in X and Y directions which projects a target for alignment in X and Y directions (vertical and lateral directions) from a direction of a visual axis of the eye E. Near infrared light emitted from a point light source 46 passes through a relay lens 47, the half mirror 31, the beam splitter 21 and then the lens 20, thereby becoming generally parallel light. Thereafter, the light is reflected by the beam splitter 15 and projected onto the cornea Ec.

Reference numeral 40 is a target projection optical system for alignment in Z direction which projects a target for alignment of the apparatus in Z direction (a back and forth direction, a working distance direction) relative to the eye E. The target projection optical system 40 comprises a pair of first target projection optical systems 40a and 40b disposed symmetric with respect to the optical axis L1. The target projection optical system 40 also comprises a pair of second target projection optical systems 40c and 40d disposed symmetric with respect to the optical axis L1 forming a smaller angle between their optical axes than that of the first target projection optical systems 40a and 40b. The first target projection optical systems 40a and 40b respectively include point light sources 41a and 41b, spot apertures 42a and 42b, and collimator lenses 43a and 43b so as to project a target on the cornea Ec at an infinite distance by generally parallel light. On the other hand, the second target projection optical systems 40c and 40d respectively include point light sources 41c and 41d so as to project a target on the cornea Ec at a finite distance by divergent light.

Reference numeral 50 is a detection optical system for detecting images of each alignment target. Each image of alignment targets formed on the cornea Ec is reflected by the beam splitter 15 and then passes through an objective lens 51 and a mirror 52 to be photographed by a CCD camera 53.

Control System

Picture signals from the camera 53 are inputted to an image processing unit 77. The image processing unit 77 conducts a predetermined process on the inputted image signals and send the processed image signals to a control unit 70. Based on the signals from the image processing unit 77, the control unit 70 obtains positions of each alignment target image, a position of a pupil and the like.

Reference numeral 110 is an X driving system, 100 is a Y driving system, and 120 is a Z driving system for respectively moving the measurement unit 4 in X, Y and Z directions relative to the main body 3.

Figure 3:
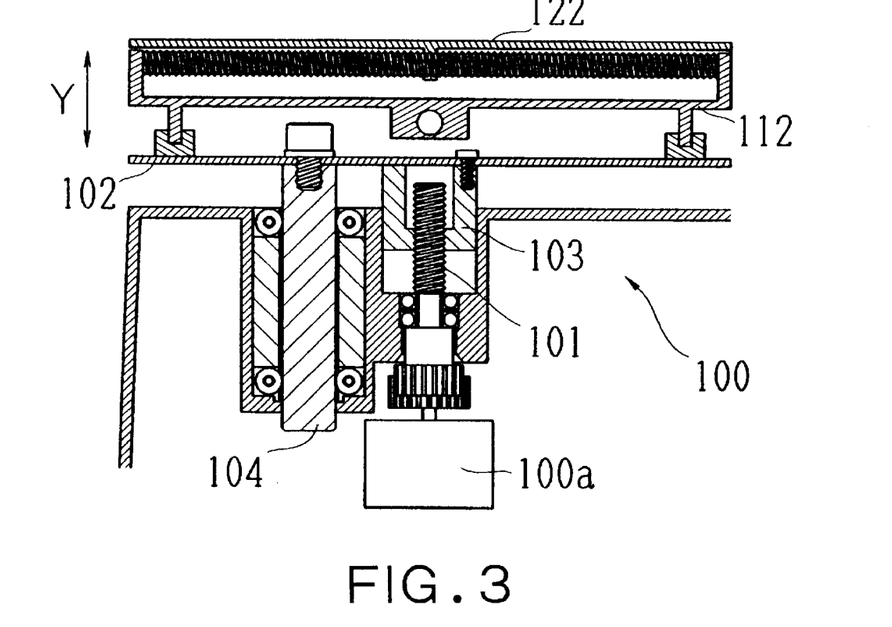
FIG. 3 is a view showing a Y driving system of the apparatus shown in FIG. 1.
Figure 4:
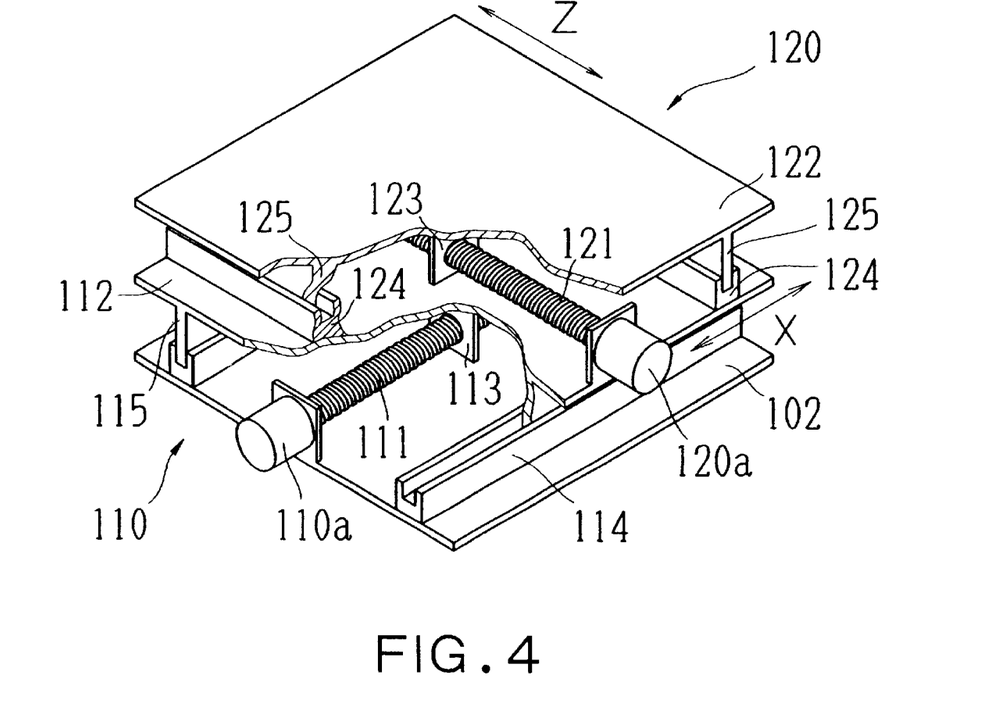
FIG. 4 is a view showing an X driving system and a Z driving system of the apparatus shown in FIG. 1.

The Y driving system 100 (see FIG. 3) rotates a feed screw 101 by a pulse motor 100a fixedly provided to the main body 3, thereby causing a female screw portion 103 fixedly provided to a Y table 102 to descend and ascend. As the result, the Y table 102 moves vertically. 104 is a guide shaft fixed to the Y table 102. The X driving system 110 (see FIG. 4) rotates a feed screw 111 by a pulse motor 110a fixedly provided to the Y table 102, thereby causing a female screw portion 113 fixedly provided to an X table 112 to move right and left. As the result, the X table 112 moves laterally. 114 is a guide groove fixedly provided to the Y table 102, and 115 is a guide plate fixedly provided to the X table 112. The Z driving system 120 (see FIG. 4) has a configuration similar to the X driving system 110, and through rotation of a feed screw 121 by a pulse motor 120a fixedly provided to the X table 112, a female screw portion 123 fixedly provided to the Z table 122 is moved back and forth. As the result, the Z table 122 moves back and forth. 124 is a guide groove fixedly provided to the X table 112, and 125 is a guide plate fixedly provided to the Z table 122. Each of these driving systems 100, 110 and 120 allows the measurement unit 4 mounted on the Z table 122 to move in each of X, Y and Z directions.

Figure 5:
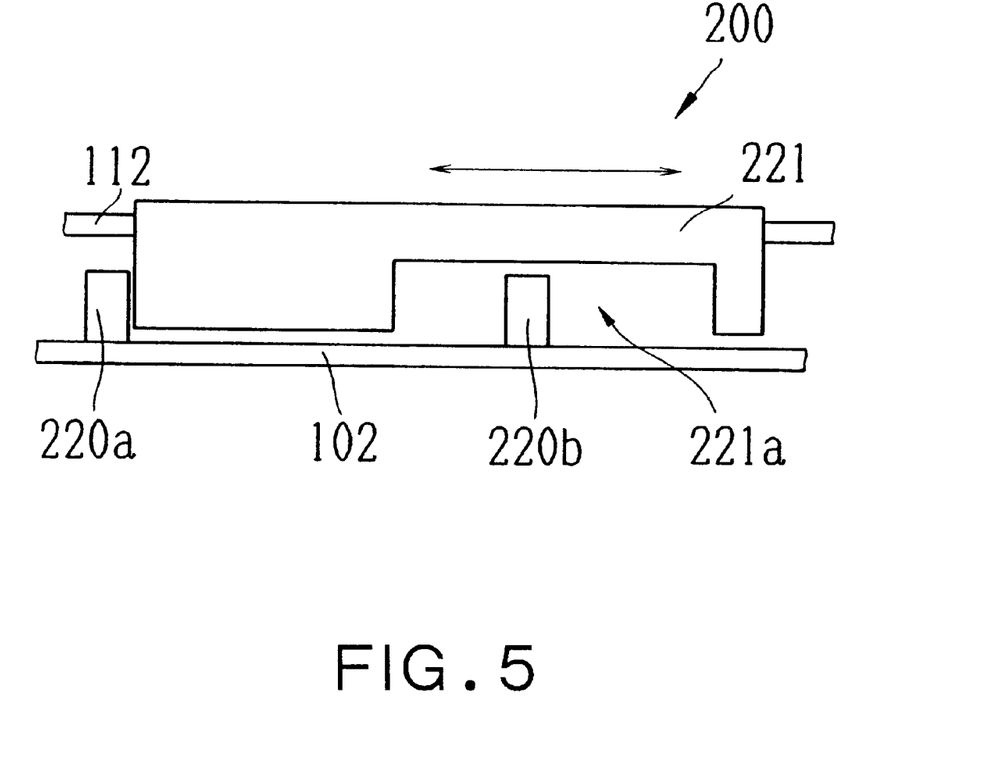
FIG. 5 is a view showing a travel position detecting mechanism of a measurement unit.

In addition, each of the driving systems 100, 110 and 120 is provided with a travel position detecting mechanism 200 for detecting an original position and a movement limit regarding each of X, Y and Z directions. The travel position detecting mechanism 200, for example, for X direction is provided with photosensors 220a and 220b fixed to the Y table 102, and also with a shielding plate 221 having a notch portion 221a fixed to the X table 112 (see FIG. 5). The photosensor 220a detects the original position from the timing of change in a shielding condition caused by an edge of the shielding plate 221, and detects in which direction the X table resides based on the detected shielding condition. The photosensor 220b detects the movement limits at the both sides from change in a shielding condition of the notch portion 221a caused by the movement of the shielding plate 221. The original position and the movement limits in Y direction and Z direction are detected using the configuration similar to that of X direction detection (description thereof is omitted).

The original position of the measurement unit 4 in X direction is set at a center of the main body 3. In addition, the initial position of the measurement unit 4 is set at a shifted position from the center of the main body 3 in a direction of a right eye by half an average interpupillary distance (for example, 64 mm/2=32 mm). This initial position setting allows a measurement to be started from the right eye promptly. The original position and the initial position in Y direction are set at the center of the movable range. The original position and the initial position in Z direction are set at the farthest side from the eye E in order to avoid contact between the eye E and the measurement unit 4.

Besides the components described above, a printer 6, a communication control unit 7, a memory 8, a power circuit 80 and the ID card reader 9 are connected to the control unit 70. A battery 81 is connected to the power circuit 80, and a data collecting device 300 such as a computer is connected to the communication control unit 7.

Figure 6:
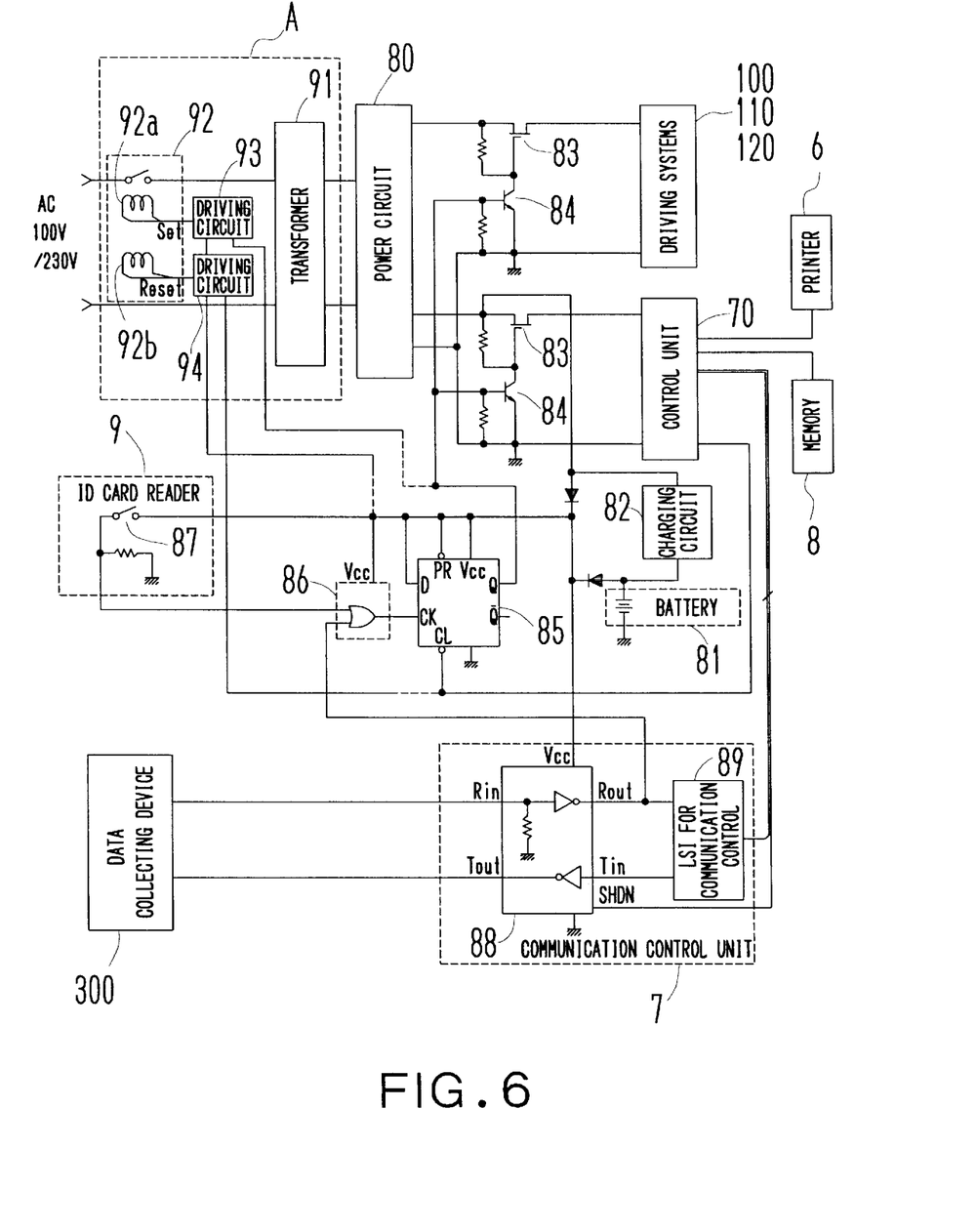
FIG. 6 is a view showing an exemplary circuit for controlling power supply.

FIG. 6 is an exemplary circuit for controlling power supply. The circuit is constituted using an FET 83, a transistor 84, a D flip-flop 85, an OR circuit 86 and the like. 82 is a charging circuit for charging the battery 81. The card reader 9 has a switch 87, and the communication control unit 7 has an RS-232C transceiver 88 as well as an LSI for communication control 89.

Description is now given to operations of the apparatus having a configuration as above.

When starting an examination (a measurement), the examinee inserts his ID card into the card reader 9. Once the ID card is inserted into the card reader 9 (once the card reader 9 is in a state of readiness to read data stored in the ID card), the switch 87 is turned on, the OR circuit 86 is given a signal which is held HIGH, and a CK terminal of the D flip-flop 85 is driven HIGH resulting in a HIGH output terminal Q. As the result, the transistor 84 and the FET 83 cause power to be supplied to the power circuit 80 and the following circuits, thereby putting the control unit 70, each of the driving systems 100, 110 and 120, and the other circuits into an active mode (in other words, the main power is turned on). Here, when power supply to the power circuit 80 and the following circuits is being suspended (when the active mode is not established), a power save mode works, in which power is supplied from the battery 81 to the OR circuit 86, D flip-flop 85, and to the transceiver 88.

When the main power is on (when in the active mode), the control unit 70 executes initialization of each operating unit. In the fixation target optical system 30, the lens 32 is temporarily moved left as seen in FIG. 2, and the photosensor 65 confirms the original position. Thereafter, the motor 61 is rotated for an amount corresponding to a predetermined number of pulses to move the lens 32 back to its initial position. As shown in FIG. 2, the initial position of the lens 32 is set at the center of the movable range which is a position corresponding to 0 diopter (0 D) with consideration of plus or minus in a refractive power of the eye.

In addition, initialization of each of the driving systems 100, 110 and 120 is executed. In the X driving system 110, the measurement unit 4 is moved in a direction where the edge of the shielding plate 221 may be detected by the photosensor 220a. After confirming the original position by the photosensor 220a, the motor 110a is driven for an amount corresponding to a predetermined number of pulses to move the measurement unit 4 to the initial position for right eye measurement. Similarly, the Y driving system 100 and the Z driving system 120 move the measurement unit 4 to the initial position.

When the initialization is completed, the apparatus is in a state of readiness to start a visual acuity test. The examinee then places his chin on a chin rest 2a mounted to the head support unit 2. Thereafter, the examinee operates the joystick 5 to roughly make alignment such that the right eye can see the fixation target presented inside the measurement unit 4 through a measurement window 4a. If the joystick 5 is tilted to right and left, the control unit 70 issues signals to drive the X driving system 110 in a manner to move the measurement unit 4 in X direction. If the joystick 5 is tilted back and forth, the control unit 70 issues signals to drive the Y driving system 100 in a manner to move the measurement unit 4 in Y direction.

Once each image of the alignment targets projected on the cornea Ec is detected by the apparatus (the camera 53) through making alignment roughly in X and Y directions, the control unit 70 drives the each of the driving systems 100, 110 and 120 thereby performing auto alignment. That is to say, the control unit 70 drives the X driving system 110, the Y driving system 100 based on information about the detected target image that is projected by the light source 46 and that is located at the center of all the alignment target images, thereby making precise alignment in X and Y directions automatically. In addition, after the target image projected by the light source 46 is brought into a detectable condition, the control unit 70 drives the Z driving system 120 to make precise alignment in Z direction automatically. The alignment condition in Z direction is judged thorough comparison of the height of the target images at an infinite distance projected by the projecting optical systems 40a and 40b with the height of the target images at a finite distance projected by the projecting optical systems 40c and 40d (through comparison of the distance between the target images). This judgement is made using the following characteristic: in the case of projecting targets at an infinite distance and at a finite distance, the height of (distance between) the target images at an infinite distance remains unchanged, while the height of (distance between) the target images at a finite distance changes in response to the change in the working distance (See U.S. Pat. No. 5,463,430 (Japanese Unexamined Patent Publication No. HEI 6-46999)). Once the alignment condition in each direction is all brought in a predetermined acceptable range, the control unit 70 automatically generates a trigger signal to perform the measurement.

The target of the target plate 13 illuminated by the light sources 11 is projected onto the eye E, and the image of the target reflected by a fundus Ef is detected by the photodetector 27. The control unit 70 moves the target plate 13 together with the lens 25 to a conjugate position with the fundus Ef based on photo-receptive signals of the reflected light detected by the photodetector 27. Next, the control unit 70 drives the motor 61 to move the lens 32 so that the eye E is fogged by adequate diopters. Thereafter, the control unit 70 rotates the light sources 11 and the photodetector 27 180° on their optical axes. During the rotation, the target plate 13 moves in response to the photo-receptive signals from the photodetector 27, and an not-illustrated potentiometer detects the movement amount. The control unit 70 obtains values of refractive power in each meridian from the result of detection by the potentiometer, and then conducts a predetermined process on the thus obtained refractive power so as to obtain refractive power data of the eye E.

After completing the measurement of the right eye, the measurement unit 4 is moved to a position for a left eye measurement. Here, the movement amount may be set at an average interpupillary distance of 64 mm or the like. In the case where the examinee can not see the fixation target with his left eye even after moving the measurement unit 4, the examinee operates the joystick 5, similarly to the case of right eye, to make rough alignment so that the examiner can see the fixation target presented inside the measurement unit 4 with his left eye. Thereafter, the control unit 70 completes precise alignment (auto alignment) based on the detection information about the target images sent from the image processing unit 77 and performs a measurement automatically.

Once the measurement results on the both eyes are obtained, the control unit 70 prints out the measurement data from the printer 6 as well as to outputs (transmits) the measurement data and the ID of the examinee to the data collecting device 300 via the communication control unit 7. After confirming that the measurement data from the apparatus 1 is properly received (or properly recorded), the data collecting device 300 transmits (transmits back) a signal indicating completion of receiving data to the apparatus 1. Here, in order to confirm whether the measurement data has been properly received, data for checking data integrity such as check sum may be added to the data to be transmitted.

Once the measurement data and the ID of the examinee are transmitted from the communication control unit 7 to the device 300 and the signal indicating completion of receiving data is received by the transceiver 88, the signal is interpreted by the control unit 70 via the LSI 89, whereby it is determined that the data transmission (or recordation of the data by the device 300) has been completed. Being triggered by this, the control unit 70 makes the CL terminal of the D flip-flop 85 LOW, and the transistor 84 and FET 83 suspend power supply to the power circuit 80 and the following circuits (the power save mode is established). As described above, especially in the case of the apparatus intended to be operated for measurement by the examinee himself, if the apparatus is put into the power save mode at ordinary times (when the apparatus is not in use) and the main power is turned on (the apparatus is put into the active mode) only when the apparatus is in use, power consumption can be reduced and lifetime of the components can be extended.

Further, when the power is supplied to the power circuit 80 and the following circuits (when the apparatus 1 is in the active mode), the OR circuit 86, the D flip-flop 85 and the transceiver 88 are supplied power from the power circuit 80. In addition, the battery 81 is charged by the charging circuit 82.

Still further, the apparatus 1 may be triggered to go into the active mode when an activation command signal from the device 300 is received by the transceiver 88 of the communication control unit 7, instead of when the switch 87 of the card reader 9 is turned on (when the ID card is inserted) as described above.

Still further, the apparatus 1 may be triggered to go into the power save mode when the switch 87 of the card reader 87 is turned off (when the ID card is removed), instead of when the transceiver 88 receives the signal indicating completion of receiving data from the device 300.

Still further, it is also possible that the apparatus 1 is triggered to go into the power save mode when the measurement data is stored into the memory 8 or when the measurement data is printed out by the printer 6.

Still further, the measurement data may be stored not in the data collecting device 300 but in the ID card provided that a card reader/writer is used instead of the card reader 9. The active mode may be triggered when the ID card is inserted or when the ID card is read out, and the power save mode may be triggered when the ID card is removed or when the measurement data is written to the ID card.

Still further, in the above description, main power on the secondary side of the power circuit is opened/closed. Yet, by opening/closing the primary side of the power circuit, power can be saved further. As shown in the dotted square A in FIG. 6, a latching relay 92 is disposed on the power line of the primary side that is the side upstream from a transformer 91, and its Set coil and Reset coil are driven by respective driving circuits. Each coil is capable of making the relay contact ON/OFF by passage of pulsed current. The output terminal Q of the D flip-flop 85 is connected to a Set coil driving circuit 93, and the control unit 70 and a CL terminal of the D flip-flop are connected to a Reset coil driving circuit 94. In this case, the above-described circuits for opening/closing the power lines on the secondary side are no longer necessary.

Although the above preferred embodiment exemplary describes communications using RS-232C, it goes without saying that other cable communications or wireless communications are as well applicable.

Further, although the above preferred embodiment exemplary describes the auto visual acuity testing apparatus, it is needless to say that the present invention is as well applicable to other ophthalmic apparatuses. Moreover, the present invention is applicable to diagnosing apparatuses other than ophthalmic apparatuses.

As has been described above, the present invention can improve operability for initiating and suspending power supply. In addition, the present invention is capable of saving energy more effectively as well as extending lifetime of the components.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A diagnosing apparatus for examining or measuring a body of an examinee, the apparatus comprising:

diagnosing means for examining or measuring the body of the examinee, the diagnosing means including a driving system and a control unit which controls the driving system;

a main circuit through which electric power of a power supply is supplied for the driving system and the control unit to run the driving system and the control unit;

data read means for reading out data from a storage medium, the data being individual to the examinee or to an examiner;

condition detecting means for detecting whether or not the data is in a readable condition; and a power supply signal sending circuit having a battery and being actuated by electric power of the battery when the electric power of the power supply is not supplied, the power supply signal sending circuit starting supply of the electric power of the power supply for the main circuit when the data is in the readable condition.

2. The diagnosing apparatus according to claim 1, wherein the data read means is included in a card reader for reading out the data from a card as the storage medium, and the condition detecting means determines a condition that the card is being inserted into the card reader as the readable condition.

3. The diagnosing apparatus according to claim 1, further comprising:

storage means for storing diagnostic data obtained by the diagnosing means; and storage completion detecting means for detecting whether or not the diagnostic data has been stored in the storage means, and wherein the power supply signal sending circuit stops supply of the electric power of the power supply for the main circuit when the diagnostic data has been stored.

4. The diagnosing apparatus according to claim 3, further comprising transmission means for transmitting the diagnostic data to a data collecting device that includes the storage means, and wherein the storage completion detecting means includes receive means for receiving a receive completion signal from the data collecting device, and determines that the diagnostic data has been stored upon receiving the receive completion signal.

5. The diagnosing apparatus according to claim 1, further comprising:

output means for outputting diagnostic data obtained by the diagnosing means; and output completion detecting means for detecting whether or not the diagnostic data has been outputted by the output means, and wherein the power supply signal sending circuit stops supply of the electric power of the power supply for the main circuit when the diagnostic data has been outputted.

6. The diagnosing apparatus according to claim 1, further comprising data write means for writing diagnostic data obtained by the diagnostic means in the storage medium, and wherein the condition detecting means detects whether or not the diagnostic data has been written, and the power supply signal sending circuit stops supply of the electric power of the power supply for the main circuit when the diagnostic data has been written.

7. The diagnosing apparatus according to claim 6, wherein the data read means and the data write means are included in a card reader/writer that reads out the data from, and writes the data into a card as the storage medium, and the condition detecting means determines a condition that the card is being inserted into the card reader/writer as the readable condition and a condition that the card is being removed from the card reader/writer as a written condition.

8. A diagnosing apparatus for examining or measuring a body of an examinee, the apparatus comprising:

diagnosing means for examining or measuring the body of the examinee, the diagnosing means including a driving system and a control unit which controls the driving system;

a main circuit through which electric power of a power supply is supplied for the driving system and the control unit to run the driving system and the control unit;

storage means for storing data on the examinee;

detecting means for detecting whether or not diagnostic data obtained by the diagnostic means has been stored in the storage means; and a power supply signal sending circuit having a battery and being actuated by electric power of the battery when the electric power of the power supply is not supplied, the power supply signal sending circuit stopping supply of the electric power of the power supply for the main circuit when the diagnostic data has been stored.

9. The diagnosing apparatus according to claim 8, further comprising transmission means for transmitting the diagnostic data to a data collecting device that includes the storage means, and wherein the detecting means includes receive means for receiving a receive completion signal from the data collecting device, and determines that the diagnostic data has been stored upon receiving the receive completion signal.

10. A diagnosing apparatus for examining or measuring a body of an examinee, the apparatus comprising:

diagnosing means for examining or measuring the body of the examinee, the diagnosing means including a driving system and a control unit which controls the driving system;

a main circuit through which electric power of a power supply is supplied for the driving system and the control unit to run the driving system and the control unit;

output means for outputting diagnostic data on the examinee;

detecting for detecting whether or not the diagnostic data obtained by the diagnosing means has been outputted by the output means; and a power supply signal sending circuit having a battery and being actuated by electric power of the battery when the electric power of the power supply is not supplied, the power supply signal sending circuit stopping supply of the electric power of the power supply for the main circuit when the diagnostic data has been outputted.

11. The diagnosing apparatus according to claim 10, wherein the output means includes a printer for printing out the diagnostic data.

12. The diagnosing apparatus according to claim 10, wherein the output means includes transmission means for transmitting the diagnostic data to a data collecting device.

* * * * *

UNITED STATES PATENT AND TRADEMARK OFFICE
CERTIFICATE OF CORRECTION

PATENT NO.   : 6,511,181 B1
DATED        : January 28, 2003
INVENTOR(S)  : Masanao Fujieda It is certified that error appears in the above-identified patent and that said Letters Patent is hereby corrected as shown below:

<u>Column 10,</u>
Line 39, "detecting for" should read -- detecting means for --.

Signed and Sealed this

Third Day of June, 2003

JAMES E. ROGAN
*Director of the United States Patent and Trademark Office*